United States Patent [19]

Albarella et al.

[11] Patent Number: 4,898,813

[45] Date of Patent: Feb. 6, 1990

[54] CATALYTIC TEST COMPOSITION INTENDED TO PRODUCE A RANGE OF COLORS

[76] Inventors: James P. Albarella, 25845 Meadow Oak La.; Steven C. Charlton, 1533 Strong Ave.; James W. Reinsch, 3421 Whitfield Ct.-D, all of Elkhart, Ind. 46514; Mary E. Warchal, 10272 Jefferson Rd., Osceola, Ind. 46561

[21] Appl. No.: 848,691

[22] Filed: Apr. 4, 1986

[51] Int. Cl.$^4$ .................... C12Q 1/00; C12Q 1/26; C12Q 1/54; C12Q 1/60

[52] U.S. Cl. .................... 435/4; 422/55; 422/56; 435/11; 435/14; 435/15; 435/19; 435/25; 435/26; 435/28; 435/805; 436/800; 436/805

[58] Field of Search .............. 435/4, 11, 14, 15, 18, 435/25, 26, 28, 805, 19; 422/55–57; 436/800, 805

[56] References Cited

U.S. PATENT DOCUMENTS

| | | | |
|---|---|---|---|
| 4,460,684 | 7/1984 | Bauer | 435/805 |
| 4,490,465 | 12/1984 | Limbach et al. | 435/805 |
| 4,547,461 | 10/1985 | Esders et al. | 422/57 |
| 4,629,697 | 12/1986 | Limbach et al. | 422/56 |
| 4,654,310 | 3/1987 | Ly | 435/805 |

OTHER PUBLICATIONS

McGiluray et al, *Meth. Enzymol. XVIIB*, 585–586, 1971.
*Worthington Enzyme Manual*, Worthington Biochemical Corporation, Freehold, NJ, 1972, p. 17.

*Primary Examiner*—Sam Rosen
*Assistant Examiner*—David A. Saunders
*Attorney, Agent, or Firm*—Roger N. Coe

[57] ABSTRACT

Test compositions and test devices are provided which are capable of generating different hues at different analyte concentrations. Visual results for clinically important analytes, such as glucose and cholesterol, are provided by use of compositions containing two independent catalytic systems which are reactive with a common substrate generated from the analyte of interest, to produce visual endpoints of different hues for different concentrations of analyte. Preferred formulations provide a RAINBOW of hues, the particular final hue produced depending on the concentration of the analyte.

19 Claims, No Drawings

CATALYTIC TEST COMPOSITION INTENDED TO PRODUCE A RANGE OF COLORS

FIELD OF THE INVENTION

The invention relates to test compositions and test devices capable of generating different hues at different analyte concentrations. Visual tests for clinical analytes are the focus of the invention.

UTILITY

Colorimetric tests are conveniently used as visual tests with which relatively untrained personnel can routinely obtain results by simple comparison to an appropriate color chart. Visual tests are inexpensive and convenient since no instrumentation is required. Presently, visual tests are used for routine screening of urine samples for a number of diagnostically important analytes, used by diabetics for home testing of urine or blood glucose and used in other fields, for example water testing for iron content.

However, currently available visual tests relate the intensity of a particular color to the concentration of analyte. For example, a test device may change from colorless to light blue to darker shades of blue with increasing concentration of glucose. Greater visual discrimination, and therefore greater accuracy, is possible, when a range of colors is provided rather than different shades of a single color. Therefore a test composition which exhibits different colors (or hues) at different analyte concentrations would be easier to use and would provide more accurate visual results.

In order to allow visual differentiation of higher concentrations of glucose, many currently available products resort to the use of two reagents pads, one of which provides better color differentiation at the higher concentration range. Otherwise such products would exhibit only very slightly differing shades of dark blue (or dark green) above 150 mg/dL glucose. In contrast, a test device of this invention can produce dramatic color changes, blue to sea green to light yellow to red, over a range of 0 to 800 mg/dL glucose.

This invention provides compositions which allow the control of the production of a range of hues, especially for clinically important analytes.

INFORMATION DISCLOSURE

U.S. Pat. No. 4,490,465 discloses a test system for the determination of glucose having an extended range of measurement. The system contains at least one pyridine linked dehydrogenase and one non-pyridine linked dehydrogenase. However the indicators produced are said to be in equilibrium. Therefore, their reaction and subsequent color change could not be independently controlled.

DE 32 11 167 claims at least two enzymes systems each of which is independently capable of catalyzing the direct or indirect conversion of a substrate. The specification defines "independent of one another" to mean that, in the simultaneous presence of the systems that react with the substrate, the reaction through the second system takes place only after the coenzyme of the first system has been largely consumed.

DE 32 47 894 discloses a test system for the determination of NAD(P)H or substrates or enzymes reacting under the formation or consumption of NAD(P)H characterized in that it contains a single enzyme system which can react with several substances with different electrochemical potentials, in the presence of NAD(P)H. The color formation is controlled by the electrochemical potentials of the substances used and the system cannot be altered to produce different colors at different analyte concentrations except by finding substances having different electrochemical potentials. Particular examples of electron acceptors include dichlorophenolindophenol and INT, (2-(4-iodophenyl)-3-(4-nitrophenyl)-5-phenyltetrazolium chloride). The specification states that the test system can be impregnated into absorbent materials. A yellow component is added to the color seen by the incorporation of a background dye, titanium yellow.

Japanese Patent Application 59-106299 was published June 19, 1984. The application discloses a method for estimating NAD(P)H with oxidized glutathione in the presence of glutathione reductase and a color forming agent. Examples of color forming agents given are 5,5'-dithiobis(2-nitrobenzoic acid); N-(1-anilino-naphthyl-4)maleimide; Beta-hydroxyethyl-2,4-dinitrophenyldisulfide; 2,2-dithiopyridine; and benzimidazolyl maleimide.

European Patent Application 0-153-872 discloses a method for the determination of the reduced form of nicotinamide adenine dinucleotide phosphate which involves reacting NAD(P)H with (1) peroxidase or thiol oxide reductase and (2) diaphorase or an electron carrier in the presence of a chromogen and determining the pigment thus formed. These two reactions do not act on a common substrate.

None of these disclosures provide test compositions composed of two independent catalytic systems capable of generating changes in hue independently.

SUMMARY OF THE INVENTION

The invention provides a test composition for the visual determination of the concentration of an analyte in fluid sample, comprising: (a) a common substrate generating system capable of generating a common substrate by reaction with an analyte of interest; (b) a first independent catalytic system capable of generating a change in hue in a first indicator component by reaction with the common substrate; and, (c) a second independent catalytic system capable of generating a change in hue in a second indicator component by reaction with the common substrate; whereby the generation of the change in hues of the first and second indicator components can be controlled to provide different hues at different analyte concentrations, the particular final hue produced by the test composition depending on the concentration of the analyte. The change in hues of the first and second indicator components of the two independent systems occurs substantially simultaneously.

The composition can be dissolved to provide a test solution or incorporated in a carrier matrix to provide a test device format. The use of compartmentalization to prepare a test device is preferred.

DESCRIPTION OF THE INVENTION

Visual color matching is convenient and it can provide an acceptably accurate determination of analyte concentration without the need for expensive instrumentation. Color can be broken into components such as saturation, lightness and hue. Hue is commonly referred to as "color" e.g., whether something "looks" blue, red or yellow. Throughout the specification the term "hue" is used.

Generally one hue is associated with one form of a single indicator. Therefore in order to generate a range of hues, a number of different indicator molecules are required. The possible changes of hue are numerous. An indicator can change from one hue to another, one hue to colorless or from colorless to a hue. It is even possible that the indicator itself will not change but that the format of a device incorporating the test composition is such that there is an apparent change in hue of the device when contacted with a test sample containing the anaylte. For example, the hue of the indicator could not be seen prior to the reaction of the test composition with the analyte but is visible after that reaction occurs. Because it is desirable that the change of final hue exhibited by the test device from one analyte concentration to another be as clear to the user as possible; the changes, colorless to a hue and a hue to colorless, have been preferred. When using two or more indicators, at least one indicator component is preferably changed from one hue to colorless. Otherwise the final hue of the test composition or device will move toward black as more hues are produced. While a composition containing two indicator components can be used, the use of three indicator components has been found to be advantageous.

It is particularly desirable to control the production and/or disappearance of indicators which in one form exhibit one of the primary hues: red, yellow, blue.

For example, consider a test composition containing indicators which exhibit the following change in hue in the order shown.

indicator (1) blue to colorless
indicator (2) colorless to yellow
indicator (3) colorless to red If the indicators react in sequence, the apparent final hue of the test composition would be blue to colorless to orange (yellow+red).

However, if indicator 2 changed hue concurrently with indicator 1, the change in indicator 3 occurring later; the apparent final hue of test composition would be blue to green (blue+yellow) to yellow to orange (yellow+red) to red.

A similar example is:
indicator (1) red to colorless
indicator (2) colorless to yellow
indicator (3) colorless to blue If the indicators reacted in sequence the apparent final hue of the test composition would be red to colorless to yellow to green (blue+yellow). If the indicators reacted as described above, with two indicator changes being produced simultaneously the third change being delayed, the apparent hue of the test composition would be red to orange (red+yellow) to yellow to green (yellow+blue) to blue.

Both of these schemes containing simultaneous hue changes could produce a full spectrum RAINBOW. Such a RAINBOW would be desirable because it would provide the widest range of hues visible to the eye.

The problem is twofold: (1) to select the indicators having changes in hue induced independently to give the maximum change in hue, and; (2) to ensure that these indicators react in an orderly fashion depending only on the concentration of the analyte.

It has been found that a controlled range of hues can be produced by using two independent catalytic systems, each reactive with a common substrate to produce changes in hue of one or more indicator components. The systems are chosen such that the indicator(s) in one system are not in equilibrium with the indicator(s) in the other system during the time of the assay. Therefore, the final hue produced by the test composition when contacted by a particular analyte concentration can be controlled by the activities of the independent catalytic systems. The final hue produced can be controlled by the relative increase or decrease of concentrations of the components and catalyts in the test composition.

Each independent catalytic system is a system capable of generating one or more changes in hue or changes in apparent hue. Each system reacts with a common substrate. The common substrate is usually some pivotal substrate which participates in many catalytic reactions. For example, the common substrate can be reduced nicotinamide adenine dinucleotide, NADH; adenosine triphosphate, ATP; hydrogen peroxide, $H_2O_2$; glycerol; or any other moiety which can be produced from the analyte of interest and can participate in two independent reactions to produce changes in hue.

The terms catalyst and catalytic are used in their conventional sense herein. A "catalytic" reaction is a reaction in which the rate is changed by the addition of a "catalyst" but the catalyst itself is unchanged. The catalytic reactions referred to herein are usually enzymatic but can also include nonenzymatic reactions such as those catalyzed with phenazine methosulfate. The term "independent" means that the indicator components undergoing a change in hue in one catalytic system are not in equilibrium with the indicator component(s) undergoing change in the other catalytic system during the assay time involved.

The common substrate is generated from the analyte of interest by a common substrate generating system which is usually enzymatic. Table 1 shows analytes of clinical interest and useful enzymatic systems which can provide a common substrate for this test. These reactions, and the reaction components required, are well known and are presently the basis for many diagnostic reactions which generate changes in intensity of a single hue in response to analyte concentration.

TABLE 1

| Analyte | | Common substrate |
|---|---|---|
| glucose | glucose oxidase | $H_2O_2$ or $FADH_2$ |
| | glucose dehydrogenase | NADH |
| | hexokinase/glucose-6-phosphate dehydrogenase | NADH |
| cholesterol | cholesterol oxidase | $H_2O_2$ |
| | cholesterol dehydrogenase | NADH |
| alcohol | alcohol oxidase | $H_2O_2$ |
| | alcohol dehydrogenase | NADH |
| triglycerides | lipoprotein lipase | glycerol |
| α-amylase | α-amylase | glucose |

Each independent catalytic system is capable of generating one or more changes in hue by reaction with the common substrate. Useful pairs of catalysts for reaction with a common substrate are shown in Table 2.

TABLE 2

| Common Substrate | Paired Catalysts |
|---|---|
| NADH | diaphorase/disulphide reductase |
| glycerol | glycerolkinase/glycerol dehydrogenase |
| glucose | hexokinase/glucose dehydro- |

| TABLE 2-continued | |
|---|---|
| Common Substrate | Paired Catalysts |
| | genase |

These systems are intended as examples only and are not to be interpreted as limiting in the invention. The components of these systems can be used to provide tests compositions which operate according to the present invention. In addition, with color retardant can be added to the test composition to delay the reaction of the common substrate with the independent catalytic systems. Compounds such as potassium ferricyanide, 1-N-ethyl-4-methylquinoline iodide and analogs thereof can act as color retardants in a system designed to react with NADH.

The reduced form of nicotinamide adenine dinucleotide, NADH, has been found to be a particularly useful common substrate. This system will be discussed in detail to show the breadth of the invention. Although this specification refers exclusively to nicotinamide adenine dinucleotide, NAD, and its reduced form, NADH; it is to be understood that the disclosure applies equally to the phosphorylated forms NAD(P) and NAD(P)H.

When the common substrate is NADH, the first catalytic system contains at least an oxidized first indicator component and a catalyst capable of facilitating the reaction between NADH and the oxidized first indicator component to generate a change in hue of the first indicator component. Catalytic systems useful for the common substrate NADH, based on diaphorase or catalysts having diaphorase like activity such as phenazine methosulphate and 1-methoxyphenazine methosulphate, are preferred for the first catalytic system.

The diaphorase system has been found to be useful because two oxidized indicators are readily available which exhibit distinct changes in hue. DCIP, 2,6-dichloroindophenol, is a blue compound which is reduced to a colorless form in the presence of diaphorase and NADH. INT, 2-(4-iodophenyl)-3-(4-nitrophenyl)-5-phenyltetrazolium chloride, is a colorless compound in the oxidized form which becomes red when reduced in the presence of diaphorase and NADH. The two changes in hue are sequential. Other indicators reactive with diaphorase and NADH can be used. For instance N-(2,3-dimethyl-5-oxo-1-phenyl-3-pyrazolin-4-yl)-2-chloro-6-sulfo-4-iminobenzoquinone, referred to for convenience as TR-1, and p-nitroblue tetrazolium choride, referred to herein as NBT, can be substituted for DCIP and INT. Other indophenols and related substituted alkyl, nitro, halogen and pseudohalogen derivatives can be substituted for DCIP, as well as other indicators of similar reduction potential capable of being reduced in the presence of NADH. Other tetrazoliums can be used in place of INT. Many are known in the art and have been catalogued in reviews such as "An Introduction to the Use of Tetrazolium Salts in Quantitative Enzyme Chemistry", F. P. Altman, Koch-light Laboratories, Ltd., Colnbrook, England, 1972; and "The Chemistry of Formazans and Tetrazolium Salts", A. W. Nineham, *Chem. Rev.*, 55:355 (1955).

A second parallel pathway is provided by the second independent catalytic system based on a disulfide reductase. The disulfide reductase system includes a disulfide substrate, a reductase and a thiol indicator which can be reduced in the presence of the product produced by the reaction of NADH and the disulfide substrate as catalyzed by the substrate specific reductase. A number of reductase systems are shown in Table 3 below.

| TABLE 3 | |
|---|---|
| disulfide substrate | disulfide reductase |
| L—cystine | cystine reductase |
| oxidized glutathione | glutathione reductase |
| lipoamide | dihydrolipoamide reductase (referred to as lipoamide dehydrogenase herein) |
| protein-disulphide | protein-disulphide reductase |
| oxidized thioredoxin | thioredoxin reductase |
| CoAS—Sglutathione | CoAS—Sglutathione reductase |
| asparagusate | asparagusate reductase |

The disulfide reductase system has three components: a disulfide substrate, a disulfide reductase capable of facilitating the reaction between the disulfide substrate and NADH, and a thiol indicator which can interact with the product of the reaction between the disulfide substrate and NADH to produce the second indicator. A preferred disulfide substrate is lipoamide and analogs thereof which can be used with lipoamide dehydrogenase. The disulfide reductase system has been found to be particularly useful for introducing yellow into the range of hues generated by the test composition.

The thiol indicator is any substance which will interact with a thiol (—SH compound) to give observable color. Preferred thiol indicators are colorless indicators which become yellow upon interaction. Commonly, the thiol indicator is an oxidized indicator which is reduced in the presence of the product of the reaction between the disulfide substrate and NADH to produce a reduced second indicator which can be, but need not be, yellow. However, other types of interaction which will produce color are also contemplated. For example, thiol indicators can be chelating agents such as nitroprusside, which would interact with the product of the disulfide substrate/NADH reaction to produce a red hue. A palladium complex can also be used to generate red. A yellow hue can be generated by interaction of the thiol indicator with the product of the disulfide substrate/NADH reaction by alkylation if the product is cysteine. Alternatively a cysteine product could be reacted with noradrenochrome to produce a yellow hue.

Another general type of thiol indicator is a chromophore of the desired hue, preferably yellow, immobilized behind an opaque barrier. On reaction with the product of the disulfide substrate/NADH reaction, the chromophore is released from its attachment and is free to diffuse through the opaque barrier to a position where it is visible to an observer.

Commonly, the thiol indicators which undergo reduction are disulfide compounds. Especially preferred are analogs of 5,5'-dithiobis-(2-nitrobenzoic acid) referred to herein as DTNB, whose structure is shown below:

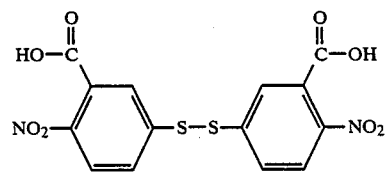

DTNB is commonly referred to as Ellman's Reagent. Changes at the carboxylic acid hydroxyl group have been found to be useful. Analogs of DTNB, which are defined herein to include positional isomers of DTNB, of the structure shown below are preferred:

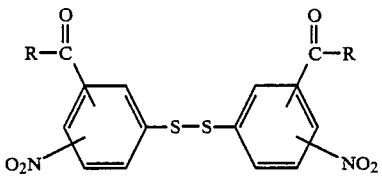

R can be many groups such as those providing an ester or amide linkage, e.g.,

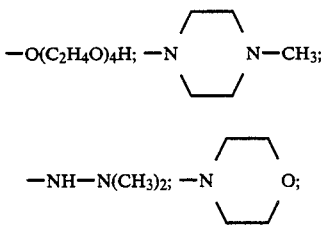

While water solubilizing groups such as those shown above are preferred in gelatin matrix formats, water insoluble analogs can be used in compartmentalized formats, which are described later in the specification.

A preferred water soluble analog compound is 3-N-(3-dimethylaminopropyl)carboxamido-4-nitrophenyl disulfide, structure shown below, whose synthesis is detailed in the examples.

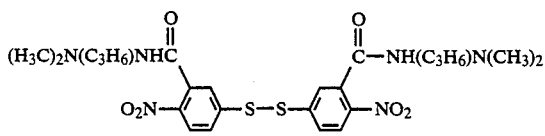

The compound is referred to subsequently in the specification as 3-ND for convenience. This compound is colorless in the oxidized form and becomes yellow in the presence of lipoamide, NADH and lipoamide dehydrogenase.

Hues of particularly useful indicators are shown in Table 4 below.

TABLE 4

|  | oxidized | reduced |
| --- | --- | --- |
| DCIP | blue | colorless |
| INT | colorless | red |
| TR-1 | red | colorless |
| NBT | colorless | blue |
| DTNB | colorless | yellow |
| 3-ND | colorless | yellow |
| EA1 | colorless | yellow |

It has been found that a color retardant can be added to the composition. The color retardant has essentially no affect on the hue visible to the user, but its inclusion can delay the catalytic affect of the independent systems, delaying the reduction of the oxidized indicators and therefore changing the final hue produced for a particular concentration of analyte. Useful color retardants include potassium ferricyanide and 1-N-ethyl-4-methylquinolinum iodide and analogs thereof or mixtures of these compounds, potassium ferricyanide being preferred. Color retardants effectively change the measurement range of the composition.

Other components such as buffers, surfactants and polymers can be added to the composition. The pH is generally chosen to give good performance and stability to the reagents and is controlled by use of buffers. The use of buffers is preferred since the enzymes function better within the pH range of about 6.0 to 8. Choice of a buffer is within the skill of the art. Useful buffers include, but are not limited to, N-2-hydroxyethyl-piperazino-N'-2-ethanesulfonic acid (HEPES), 2-[tris(-hydroxymethyl)methyl]amino ethanesulfonic acid (TES), 2-[N-morpholino]-ethanesulfonic acid (MES) and [3-(N-morpholino)propanesulfonic acid] (MOPS). Surfactants and polymers can be particularly useful in formulations containing a cationic tetrazolium salt as an oxidized indicator since surfactants such as polyoxyethylene ether, available under the trademark TRITON ® X-100 from Sigma Chemical Co., and polymers such as polyvinylalcohol and polyvinylpyrrolidone, available as PVP K30 from Aldrich Chemical Co., appear to help solubilize the cationic indicator and prevent interaction with the other indicators in the test composition. Surfactants also improve wettability of the device in a dry phase formulation. Enzyme stabilizers such as bovine serum albumin, can also be added.

Test compositions of this invention can be used by dissolving the composition in a solution or they can be incorporated into a carrier matrix and affixed to a support member such as a polyester strip to provide dry reagent strips which are well known in diagnostics. These strips provide a format which is convenient to carry and store and which is particularly useful to home users such a diabetics. Preferred compositions of this invention generate a final hue, which can be associated with a particular analyte concentration, in less than about ten minutes.

The carrier matrix employed can be any of several known in the industry, as long as the matrix can be incorporated with the composition and it does not interfere with the reactions required for the production of color. These include paper and films such as those made from natural polymers, latexes, polyurethanes, silicones or combinations of these.

In order to obtain the clearest colors possible, a clear carrier matrix is preferred. Since common analytes for this invention are water soluble compounds such as those found in body fluids, carrier matrices which can contain water, such as hydrophilic carriers, are preferred. Suitable hydrophilic carriers include agarose, gelatin, poly(vinyl)alcohol, poly(propylimine), carrageenan and alginic acid. Other carriers could be used. Mixed multilayer carriers composed of an absorbent opaque matrix, such as paper, and a hydrophilic (e.g., gelatin) carrier layer can be advantageously used when the test components are compartmentalized.

In a preferred embodiment, a solution of 1.25% carbodiimide was used to crosslink a multilayer gelatin carrier matrix. This provides a format suitable for a whole blood glucose test which allows the blood sample to be removed from the test device by wiping the surface. Other coating materials, well known in the art, can be used to allow the device to be washed or wiped to remove a colored sample if necessary.

The hydrophilic carrier layer or layers are coated onto a rigid backing or support member such as polystyrene, polyester and the like. The backing can be opaque or transparent, although an opaque white backing is commonly preferred for visually read tests.

The number and types of components, which can be used in the independent catalytic systems described previously, is increased by the use of compartmentalization of possibly incompatible components in a test device format. Compartmentalization can take on many forms. Components can be separated by placing some in a separate layer, by solubilizing within one phase of an emulsion, by precipitation, by encapsulation and so forth. Some of the available methods are described in detail in the Examples.

A multilayer gelatin carrier was preferred for compartmentalization. INT could be placed in one layer away from the other indicator components. It was also found that the position of the components in various layers could change the hue visible to the user at a particular analyte concentration and therefore afforded another means of controlling the hue generated. The apparent hue of the device can be changed by changing the order or thickness of layering.

A particular example showing the affect of compartmentalization of components in different layers on the hue visible to the user will now be described in detail.

A RAINBOW test device for the determination of glucose can be prepared with the following independent catalytic reactions:

---

NADH generating system:
glucose (analyte)
glucose dehydrogenase (enzyme)
NAD (additional component)
first independent catalytic system diaphorase (catalyst)
DCIP (oxidized first indicator, blue)
INT (oxidized third indicator, colorless)

---

DCIP was reduced by NADH first. Therefore the first independent catalytic system produces a blue to colorless then a colorless to red change in the hue visible to the user.

---

Second independent catalytic system:
lipoamide (disulfide substrate)
lipoamide dehydrogenase (disulfide reductase)
DTNB (thiol indicator, oxidized second indicator, colorless)

---

Compartmentalization of the oxidized indicators, e.g., placing the indicators in different gelatin layers, can effectively change the hue seen at different glucose concentrations even though the concentrations of test components are the same. As an example, three films were made with the indicators arranged in different layers, but keeping the concentrations of the components of the total test composition the same.

FILM A
| DCIP, DTNB, Enzymes |
| INT |

FILM B
| INT |
| DCIP, DTNB, Enzyme |

FILM C
| Enzyme |
| INT |
| DCIP, DTNB |

In gelatin, certain water soluble molecules, such as DNTB, are capable of diffusing through the gelatin after contact with an aqueous sample, while others such as INT do not readily migrate.

In Film A, glucose reacts with the enzymes. Then the NADH produced reacts with the DCIP and DTNB. However, reduction of INT is delayed until the NADH can diffuse into the lower layer of the film. At 250 mg/dL glucose, Film A is yellow orange.

In Film B, the glucose must diffuse through the INT layer before reaching the enzymes to react and produce NADH. With the production of NADH, the DCIP will be reduced but the reduction of INT is delayed since the NADH must diffuse back up onto the top layer before the INT can be reduced. Therefore, at 250 mg/dL glucose, Film B is yellow-green. The compartmentalization of INT above the enzymes and other indicator components has changed the color observed at this particular concentration of glucose.

In Film C, the glucose reacts with the enzymes in the top layer. As the NADH migrates through the INT layer, a small amount of INT reduced causing a slight red color. As the NADH migrates through to the bottom layer, the DCIP and the DTNB are reduced. Finally, since not all the NADH has reacted due to the concentration of components chosen, the NADH will react with the INT. At 250 mg/dL glucose, Film C is a reddish orange.

The ultimate goal of the invention was to generate distinctly different hues at different analyte concentrations. It has been shown that this goal can be achieved with test compositions of this invention with a variety of methods as summarized below.

(1) Choose oxidized indicators which will generate the desired hue or turn colorless upon reduction.

(2) Choose indicators for reaction in a particular catalytic system which have differing reduction potentials which will control the sequence of reactions in that system.

(3) Control the quantities of components in the independent catalytic systems so the components involved in one reaction sequence are essentially exhausted at chosen analyte concentrations.

(4) Increase (or decrease) the amount of catalyst in a system. This will increase (or decrease) the rate of interaction or reduction of the indicator components by that system and therefore change the apparent hue at a particular analyte concentration.

(5) Compartmentalize the components of the reaction system in a test device. The advantages of compartmentalization can include the ability to: change the apparent final hue of the device even when component concentrations are the same; utilize incompatible indicators or water insoluble indicators; and utilize enzyme systems normally inhibited by thiol indicators.

(6) Add a color retardant which will delay the reactions of the independent catalytic systems.

The methods suggested above can be combined.

The invention will now be illustrated, but is not intended to be limited, by the following examples:

VI. Examples

| Abbreviations | |
|---|---|
| MPMS | 1-methoxyphenazine methosulphate |
| PMS | phenazine methosulphate |
| DCIP | 2,6-dichloroindophenol |
| TR-1 | N—(2,3-dimethyl-5-oxo-l-phenyl-3-pyrazolin-4-yl)-2-chloro-6-sulfo-4-iminobenzoquinone (for preparation see Example 4A) |
| INT | 2-(4-iodophenyl)-3-(4-nitrophenyl)-5-phenyltetrazolium chloride |
| NBT | p-nitroblue tetrazolium chloride |
| DTNB | 5,5-dithiobis(2-nitrobenzoic acid) |
| 3-ND | 3-N—(3-dimethylamino propyl) carboxamido-4-nitrophenyl disulfide (for preparation see Example 4B) |
| EA1 | Dibutyl-5,5'-dithiobis-(2-nitrobenzoate acid) (for preparation see Example 4C) |
| ATP | adenosine triphosphate |
| $NAD^+$ | Nicotinamide-adenine dinucleotide, lithium salt |
| NADH | reduced nicotinamide adenine dinucleotide |
| HEPES | buffer, N—2-hydroxyethyl piperazine-N'-2-ethane sulfonic acid |
| MES | buffer, 2-(N—morpholino)-ethanesulfonic acid |
| BES | buffer, N,N—bis(2-hydroxyethyl)-2-aminoethane-sulfonic acid |
| TAPSO | buffer, 3-(N—tris(hydroxymethyl)-methylamino)-2-hydroxypropane-sulfonic acid |
| TRIS | buffer, tris(hydroxymethyl)-aminomethane |
| Triton ® X-100 | surfactant, polyoxyethylene ether available from Sigma Chemical Co. |
| GDH | glucose dehydrogenase (EC 1.1.147) capable of producing NADH |
| LipDH | lipoamide dehydrogenase |
| LDH | lactate dehydrogenase |
| U | International Units, a measure of enzyme activity (one U is the enzyme activity required to catalyze the conversion of one micromole of substrate per minute under specified conditions of temperature and pH |
| PET | polyethylene terephthalate |
| FMN | flavin mononucleotide |
| PE 310 | polyethylene coated paper |
| BSA | Bovine Serum Albumin |
| PVP K30 | polyvinylpyrrolidone, molecular weight 40,000, available from Aldrich Chemical Co. |
| dL | deciliters |
| mL | milliliters |
| μL | microliters |
| g | grams |
| mm Hg | millimeters of mercury, pressure designation |
| mp | melting point |
| μ | microns |
| RT | room temperature, usually 25° C. |

EXAMPLE 1

Varying enzyme concentration: NADH as a Common Substrate

The following example was designed to show how the final hue produced can be controlled by changing the concentrations of the enzymes. NADH was generated from the analyte glucose by a common substrate generating system composed of glucose dehydrogenase and $NAD^+$. Two independent catalytic systems react with NADH:

Pathway 1: Diaphorase/DCIP/INT
Pathway 2: LipDH/lipoamide/3-ND

Pathway 1 contains DCIP and INT which change hue from blue to colorless and colorless to red, respectively, in that order. Pathway 2 produces a yellow hue. The whole system provides the blue, green, yellow, orange, red spectrum of the RAINBOW; but the final hue produced for a particular concentration of glucose can be varied if the concentration of enzymes used is changed.

| Layer | Components | Quantity (g) | | | |
|---|---|---|---|---|---|
| | | A | B | C | D |
| 1 | Gelatin | 1.13 | 1.13 | 1.13 | 1.13 |
| | Water | 6.78 | 6.78 | 6.78 | 6.78 |
| | PVP K30 (20%) | 1.69 | 1.69 | 1.69 | 1.69 |
| | Triton ® X-100 (4%) | .40 | .40 | .40 | .40 |
| | INT | .064 | .064 | .064 | .064 |
| 2 | Gelatin | 1.13 | 1.13 | 1.13 | 1.13 |
| | Hepes buffer, 1 M pH 7.5 | 5.92 | 5.92 | 5.92 | 5.92 |
| | Water | 1.86 | 1.86 | 1.86 | 1.86 |
| | PVP K30 (20%) | 1.69 | 1.69 | 1.69 | 1.69 |
| | Triton ® X-100 (4%) | .40 | .40 | .40 | .40 |
| | 3-ND (40 mM) | 2.5 mL | 2.5 mL | 2.5 mL | 2.5 mL |
| | DCIP | 0.0147 | 0.0147 | 0.0147 | 0.0147 |
| | GDH | .060 | .060 | .060 | .060 |
| | $NAD^+$ | .060 | .060 | .060 | .060 |
| | Diaphorase (118 U/mg) | .010 | .010 | .010 | .025 |
| | Lipoamide | .030 | .030 | .030 | .030 |
| | BSA | .040 | .040 | .040 | .040 |
| | Mutarotase (5060 V/mL) | 100 μL | 100 μL | 100 μL | 100 μL |
| | LipDH (1350 U/mL) | 50 μL | 200 μL | 800 μL | 200 μL |
| 3 | Carbodiimide | 1.25% | 1.25% | 1.25% | 1.25% |

The test devices were prepared and tested as described in example 7A. The results are shown in the following table.

| Glucose mg/dL | A | B | C | D |
|---|---|---|---|---|
| 0 | medium blue | medium blue | medium blue | dark blue |
| 20 | medium blue | light blue | medium blue | dark blue |
| 40 | medium blue | light blue | light blue | dark blue |
| 70 | light blue | aqua | aqua | medium blue |
| 110 | aqua | light green | light green | aqua |
| 140 | light aqua | light green | yellow beige | light aqua |

-continued

| Glucose mg/dL | A | B | C | D |
|---|---|---|---|---|
| 180 | peach beige | light yellow-peach | yellow gold | greyish green blue |
| 250 | light rust | dirty gold | orange gold | dark peach |
| 400 | rust orange | rust orange | orange | burnt orange |
| 800 | dark rust orange | dark red rust | dark rust orange | deep red |

EXAMPLE 2:

Determination of Starch: glucose as a common substrate

A determination of starch can be made using the present invention to provide a visual endpoint of a different hue for different concentrations. Starch can be treated with amylase to generate glucose which is used as a common substrate for two independent catalytic reactions using hexokinase and glucose dehydrogenase (GDH) as enzyme catalysts. The overall reaction can be shown schematically as follows:

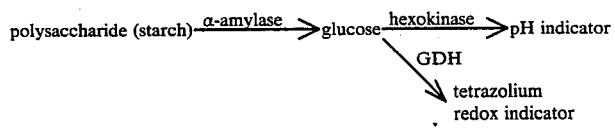

The specific independent reactions are:

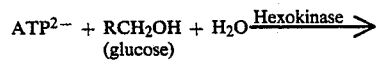

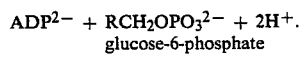

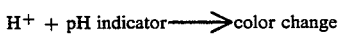

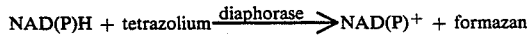

A reaction mixture was prepared by combining 0.1 mM NAD, 0.025 mM MPMS, 0.5 mM p-nitroblue tetrazolium, 0.2% Triton ® X-100, 10 mM ATP, 1 mM magnesium nitrate and 0.15 phenol red, and 10.1 mM TRIS buffer. The pH of the reagent mixture was adjusted to approximately 8.5 with ammonium hydroxide. The enzymes hexokinase (2.9 U/mL) and glucose dehydrogenase (9.9 U/mL) were added.

The pH indicator changes from red to faint yellow with decreasing pH; p-nitroblue tetrazolium changes from colorless to blue on reduction with NADH.

Aliquots of the solution were treated with glucose, allowed to react 5 minutes and the hue observed. The hues obtained with different levels of glucose (which can be related to the concentration of starch) were as follows:

| glucose mg/dL | hue |
|---|---|
| 0 | mauve/red |
| 72 | pink |
| 144 | yellow |
| 288 | brown |
| 432 | darker brown |
| 576 | mauve |

The red to yellow hues corresponded to the phenol red transition expected from the hexokinase reaction and the formation of blue (resulting in the brown to mauve) corresponded to the reduction of p-nitroblue tetrazolium by the glucose dehydrogenase pathway. The results show distinct hues which can be associated with the concentration of glucose, which can be related to the concentration of starch in a sample.

EXAMPLE 3

Glycerol as a common substrate

Another common substrate, glycerol, can be produced in the assay of triglycerides.

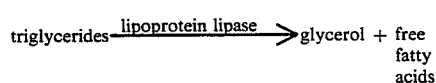

The method is analogous to that of Example 2, where a kinase and a dehydrogenase were used. Glycerol kinase and glycerol dehydrogenase work at higher pH, so the buffer used was changed to BES. The redox indicator used was DCIP (blue to colorless) and the pH indicator was phenol red (red to yellow).

A solution having the following composition was prepared:

| Reagent | NAD | Mg(NO3)2 | ATP | Buffer | Triton X-100 | phenol red | DCIP |
|---|---|---|---|---|---|---|---|
| final conc. (mM) | 0.10 | 1.0 | 1.0 | 5 | 0.1% | 0.15 | 0.15 |

The enzymes glycerol kinase (60 U/mL from E. coli, Sigma G 4509) and glycerol dehydrogenase (5.3 U/mL from cellulomonas, Sigma G 3512) were added.

The response of these solutions to glycerol at various times is shown below:

| glycerol conc. (mM) | Hue | | | | |
|---|---|---|---|---|---|
| time (min.) | 0 | 3 | 6 | 12 | 18 |
| 1 | mauve | blue | blue | blue | blue |
| 5 | mauve | blue | green | dark green | dark green |
| 10 | mauve | blue | blue/green | light green | light green |
| 15 | mauve | mauve/blue | blue | green | yellow/green |
| 20 | mauve | mauve/blue | blue/green | lime green | yellow |

EXAMPLE 4:

Preparation of Compounds

A. N-(2,3-dimethyl-5-oxo-1-phenyl-3-pyrazolin-4-yl)-2-chloro-6-sulfo-4-iminobenzoquinone (TR-1)

TR-1 is an indicator which is red in the oxidized form and is colorless upon reduction. It has a reduction potential similar to DCIP and has a been used to produce a "reverse" RAINBOW. TR-1 was prepared as follows:

Ammonium hydroxide (1N, 10 mL) was added to a mixture of 0.4 g (1.9 mmol) of 4-aminoantipyrine, and 0.5 g (1.7 mmol) 2-hydroxy-3,5-dichlorobenzene sulfonic acid disodium salt in 50 mL of water. After stirring briefly, 1.3 g (3.8 mmol) of potassium ferricyanide ($K_3Fe(CN)_6$) was added and the reaction allowed to stir at room temperature for one hour. The mixture was filtered to yield 0.2 g (21%) of a dark brown solid. The product was homogeneous on thin layer chromatography (silica gel, with 4:1 chloroform/methanol) and apparently was a mixture of alkali and ammonium salts.

Analysis: Calculated for $C_{17}H_{10}ClN_3O_5Na$: C, 47.54; H, 3.04; N, 9.72. Found: C, 46.10; H, 3.61; N, 11.00

$^1$H NMR ($D_6DMSO$) δ: 7.80–7.20 (m, 7H), 3.40 (s, 3H), 2.53 (s, 3H),

IR (KCl): 1660, 1630, 1400 cm$^{-1}$.

B. 3-N-(3-dimethylaminopropyl)carboxamido-4-nitrophenyl Disulfide (3-ND)

A water soluble analog of 5,5'-dithiobis-(2-nitrobenzoic acid) was prepared for use as a thiol indicator. This is a preferred indicator for use with the disulfide reductase system which is colorless in the oxidized form and becomes yellow on reduction. The compound, 3-ND, was prepared as follows:

A suspension containing 7.93 g of 3-carboxy-4-nitrophenyl disulfide (20 mmol), 1.2 mL of dry N,N-dimethylformamide (1.55 mmol), 11.7 mL of thionyl chloride (60.3 mmol) and 400 mL of dichloromethane ($CH_2Cl_2$) was refluxed for four hours and then was allowed to stir overnight at ambient temperature. The resulting clear solution was evaporated in vacuo (12 mm followed by 0.1 mm Hg) to a yellow solid. The residue was then placed under an argon atmosphere, dissolved in 200 mL of $CH_2Cl_2$, cooled to 0°, and then treated with 10.1 mL of 3-dimethylaminopropylamine (80 mmol). The reaction mixture became a dark orange and a precipitate was formed. The resulting solution was allowed to warm to ambient temperature overnight. The reaction mixture was then successively extracted four times with 200 mL portions of 5% sodium bicarbonate solution, twice with 200 mL of water, and once with brine. The organic layer was then dried over magnesium sulfate, filtered, and concentrated to give 9.39 g of a dark orange oil. The mixture was then flash chromatographed on 500 g of $SiO_2$—60 (70–230 mesh, available as Silica gel-60 from Merck & Co. (equilibrated and eluted with 50:10:1 dichloromethane/methanol/concentrated ammonium hydroxide solvent mixture. Fractions 110 to 205 containing the purified product were pooled and concentrated in vacuo to give 7.06 g of an orange solid. The crude product was recrystallized from ethyl acetate using a treatment with pulverized carbon black, such as norite, and a diatomaceous earth, a filtering aid available from Manville Products Corp., Denver, Colo., under the trademark Celite®. Obtained was 5.47 g of light yellow crystals after drying at 55°, 0.1 mm. Yield=48.4%. mp 152°–156°.

Analysis: Calculated for $C_{24}H_{32}N_6O_6S_2$: C, 51.05; H, 5.71; N, 14.88.

Found: C, 51.05; H, 5.56; N, 14.62.

PMR (60 MHz, $CDCl_3$) δ: 1.73 (quintet, J=6 Hz, 4H); 2.17 (s, 12H); 2.45 (t, J=6 Hz, 4H); 3.53 (q, J=6 Hz, 4H); 7.57 (s, 2H); 7.65 (dd, J=7 Hz, 2 Hz, 2H); 8.02 (m, 2H, N-H); 8.03 (d, J-7 Hz, 2H).

IR(KBr) cm$^{-1}$: 3260, 3060, 2940, 2870, 2820, 2790, 1650, 1560, 1530, 1470, 1345.

Mass Spectrum (FAB) m/e: 565 (M+1, 13.6%).

C. Dibutyl-5,5'-Dithiobis-(2-nitrobenzoate) (EA1)

This compound, which is referred to herein as EA1, is a lipophilic analog of 5,5'-dithiobis-(2-nitrobenzoic acid). It was prepared for use as a thiol indicator as follows:

A suspension containing 6.85 g (17.25 mmol) of 5,5'-dithiobis-(2-nitrobenzoic acid), 3.46 mL of thionyl chloride, 0.346 mL of N,N-dimethylformamide, and 350 mL of dichloromethane were heated to reflux for 3 hours. Additional thionyl chloride (3.46 mL) and N,N'-dimethylformamide were added and refluxing was continued for 2 hours. A clear, light green solution were obtained, indicating complete conversion to the bis-acid chloride. The solvents were removed in vacuo and the resulting light-green solid was placed under an Argon atmosphere. The residue was then suspended in 100 mL of pyridine and treated with 20 mL of n-butanol. A mild exotherm and a darkened but homogeneous reaction was obtained, which was allowed to stir overnight. The reaction solvents were removed in vacuo and the residue was dissolved in 300 mL of chloroform. The organic layer was then successively extracted thrice with 200 mL of 0.1N HCl, twice with 200 mL of 5% Na $HCO_3$ solution, and with 200 mL of brine. Drying ($MgSO_4$), filtration, and removal of solvent gave 12.79 g of an oil which was dissolved in ethyl acetate and adsorbed in vacuo onto a small amount of $SiO_2$—60. The impregnated solid was then placed atop a column of 500 g of $SiO_2$—60 (230–400 mesh) which had been packed and equilibrated with 8:1 hexane-ethyl acetate. The column was then flash chromatographed using this solvent mixture with fractions of 25 mL collected. Fractions 190–270 were pooled and concentrated to give 8.07 g of product of as an oil which solidified upon standing (92% yield).

Analysis: Calculated for: C, 51.96; H, 4.76; N, 5.08.
Found: C, 52.49; H, 4.88; N, 5.45.

PMR (60 MHz, CDCl₃) δ: 0.97 (t, J=7 Hz, 6H, CH₃—CH₂); 1.2–1.9 (m, 8H, —CH₂—CH₂—); 4.37 (t, J=6 Hz, 4H, —O—CH₂—CH₂—) 7.77 (s, 2H, C₆H); 7.83 (AB quartet, J=8 Hz, 4H, C₃H, C₄H).

IR (KBr) cm⁻¹: 1730

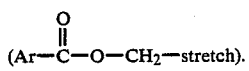
(Ar—C—O—CH₂—stretch).

Mass Spectrum: E.I. (70 EV) m/e=508 (37%, M+).

D. Dimethyl-5,5',-Dithiobis-(2-nitrobenzoate)

This compound is a lipophilic analog of 5,5'-dithiobis-(2-nitrobenzoic acid), which was prepared for use as a thiol indicator as follows:

A suspension containing 7.93 g (20 mmol) of 5,5'-dithiobis-(2-nitrobenzoic acid), 1.2 mL of N,N-dimethylformamide, 11.7 mL of thionyl chloride, and 400 mL of dichloromethane were refluxed for 4 hours until a clear light green solution was obtained. The solvents were then evaporated in vacuo to obtain a yellow solid which was then placed under an Argon atmosphere, dissolved in 200 mL of dichloromethane, and cooled to 0°. The stirred mixture was then treated with 4.03 mL of dry pyridine (50 mmol) and 30 mL of methanol. The resulting mixture was then allowed to warm to ambient temperature overnight. The reaction mixture was then successively extracted thrice with 300 mL of 5% NaHCO₃ solution, thrice with 300 mL of 1M citric acid, and 300 mL of brine. Drying (MgSO₄), filtration and removal of solvents gave 8.29 of a yellow solid which was recrystallized in two crops from toluene as a light yellow solid in 92% yield. mp 103°–104.5°.

Analysis: Calculated for: C, 45.28; H, 2.86; N, 6.60.
Found: C, 45.74; H, 3.01; N, 6.25.

PMR (60 MHz, CDCl₃) δ: 3.93 (s, 6H,

—O—CH₃);

7.8 (s, 2H, C₆H); 7.83 (AB quartet, J=8 Hz, 4H, C₃H, C₄H).

IR (KRr) cm⁻¹: 1740

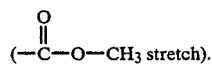
(—C—O—CH₃ stretch).

Mass Spectrum: EI (70 EV) m/e: 424.3 (M+, 67.7%).

E. 3,6-Dioxaoctyl-5,5'-Dithio-(2-nitrobenzoate)

This compound is a water soluble analog of 5,5'-dithiobis-(2-nitrobenzoic acid). It was prepared for use as a thiol indicator as follows:

A suspension containing 7.93 g (10 mmol) of 5,5'-dithio-(2-nitrobenzoic acid), 1.17 g of N,N-dimethylformamide, 11.7 mL of thionyl chloride, and 400 mL of dichloromethane was heated to reflux with stirring for 2 hours to obtain a clear solution. The solvents were removed in vacuo to give a light green solid which was placed under Argon, cooled to 0°, and suspended with stirring in 120 mL of dry pyridine. Carbitol ® (20 mL) was then added and the resulting mixture became an orangish-red homogeneous solution after 1 hour reaction time (Carbitol ® is a registered trademark of Dow Chemical Co. and is chemically named 2-(2-ethoxyethoxy)ethanol). The mixture was then allowed to come to ambient temperature overnight. The sample was then evaporated in vacuo to a dark oil and flash chromatographed on 500 g of SiO₂—60 (230–400 mesh) packed and eluted with a 0.5% methanol-chloroform solvent mixture. Fractions of 25 mL were collected. Fractions 150–186 were pooled and concentrated to give 7.86 g of a yellow oil. The sample was then dissolved in ether, treated with 4 g of Norit, filtered through Celite, and precipitated as a dense yellow oil with hexane. The solvents were then decanted and the residual solvents were removed in vacuo at 40° (0.1 mm) for 1 hour to give 5.48 g of a viscous, yellow oil (44% yield).

Analysis: Calculated for: C, 49.67; H, 5.13; N, 4.46.
Found: C, 49.41; H, 5.09; N, 4.37.

PMR (60 MHz, CDCl₃) δ: 1.2 (t, J=7 Hz, 6H, CH₃—CH₂—O—); 3.5 (q, J=7 Hz, 4H, CH₃—CH₂—O—); 3.6 (s, 8H, —CH₂—CH₂—O—); 3.8

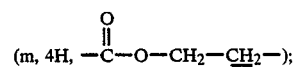
(m, 4H, —C—O—CH₂—CH₂—);

4.55

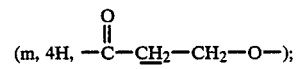
(m, 4H, —C—CH₂—CH₂—O—);

7.8 (s, 2H, C₆H); 7.82 (AB quartet, J=8 Hz, 4H, C₃H, C₄H).

IR (CHCl₃) cm⁻¹: 1740

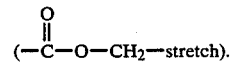
(—C—O—CH₂—stretch).

F. 3,6,9,12-Tetraoxadodecyl 5,5'-Dithio-(2-Nitrobenzoate) and 1,12-Cyclic Diester Both of these compound are water soluble analogs of 5,5'-dithiobis-(2-nitrobenzoic acid). They were prepared for use as thiol indicators as follows:

A suspension containing 7.93 g (20 mmol) of 5,5'-Dithiobis-(2-nitrobenzoic acid), 11.7 mL of thionyl chloride, and 1.2 mL of N,N-dimethylformamide was heated to reflux for 2 hours to obtain a clear yellow solution. The solvents were removed in vacuo to give a light green solid, which was dissolved in a mixture of 50 mL of dichloromethane and 5 mL of pyridine. This solution was then added slowly to a 0° solution of 34.5 mL (38.8 g, 200 mmol) of tetraethylene glycol in 100 mL of dichloromethane under an Argon atmosphere. The reaction mixture was allowed to come to ambient temperature overnight. Evaporation of solvents in vacuo gave a brown oil which was partitioned between chloroform and water. The aqueous layer was extracted again with chloroform and the combined organic layers were washed with brine and dried (Na₂SO₄). Filtration and evaporation of solvent in vacuo gave an orange oil which was flash chromatographed on 500 g of SiO₂—60 (230–400 mesh) packed and eluted with a 5% methanol-chloroform solvent mixture. Fractions of 25 mL were collected. Fractions 24–38 were pooled and concentrated to give 2.21 g of a yellow glass. This identified as the 1,12-cyclic-3,6,9,12-tetraoxaundecyl ester of 5,5'-dithiobis-(2-nitrobenzoic acid). The yield of cyclic ester was 20%.

¹³C NMR (22.5 MHz, CDCl₃) δ: 66.8, 68.3, 70.4 (all —O—CH₂—CH₂—O—); 128.8, 142.4, 146.3 (aryl C); 164.3

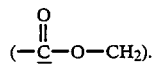

IR (CHCl$_3$) cm$^{-1}$: 1730 cm$^{-1}$

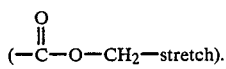

Fractions 91-101 were pooled and concentrated to give 3.94 g of the expected 3,6,9,12-tetraoxadodecyl diester. (26% yield).

$^{13}$C NMR (22.5 MHz, CDCl$_3$) δ: 61.6, 65.6, 68.3, 70.2, 70.5, 72.4 (all —O—CH$_2$—CH$_2$—O—); 129.9, 142.4, 146.5 (aryl C); 164.5

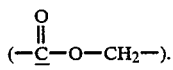

PMR (60 MHz, CDCl$_3$): integration ratio of aliphatic to aromatic protons=5.6.

IR (CHCl$_3$) cm$^{-1}$: 3600-3350 (—CH$_2$—OH stretch): 1730

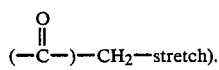

EXAMPLE 5

NADH Generating Systems Containing Enzymes Sensitive to Thiol Reagents

A general problem with a thiol detection reagent system, preferred for use with NADH as a common substrate, is that thiol indicators can react with protein systems, frequently leading to inactivation of enzyme. Many such enzyme inhibitions by DTNB are described in the literature. There are two general solutions, both involving compartmentalizing the thiol reagent: (1) sequester the thiol indicator in an organic phase or as insoluble particles; (2) physically separate the sensitive enzyme and the thiol reagent by immobilizing the latter.

A. Approach (1)-Sequestering the Reagent.

A water insoluble analog of DTNB, EA1 was used (for preparation see example 4C).

There are two approaches to sequestering the reagent: (a) EA1 was dissolved in an oil and dispersed as an emulsion in a gelatin film.

Organic Phase: EA1 (300 mM) was dissolved in tricresyl phosphate with trioctylamine (1%).

| Aqueous Phase | Final Concentration |
|---|---|
| Gelatin | 10% |
| Potassium Phosphate, pH 7.5 | 50 mM |
| DCIP | 1.5 mM |

The oil phase was emulsified with the aqueous phase in a Waring Blender to a final concentration of 5%. Lipoamide dehydrogenase (Sigma type III, 13.3 U/mL) was added to the emulsion. The emulsion was coated on a plastic support (170 μ) and dried at room temperature.

Treatment of the dried film with NADH/Lipoamide (approximately 1 mM) at pH 8.5 (tris buffer) produced a very rapid bleaching of the blue hue of DCIP and formation of yellow by the EA1 reagent. Without NADH, there was no reaction.

The enzyme lactate dehydrogenase (LDH), which is inhibited by DTNB, was tested with this film. LDH, approximately 150 U/mL, and lipoamide (approximately 1 mM) in about 250 mM lactate, pH 8.5, produced a yellow hue in about 10 minutes. The blank, without LDH, was uncolored. The conclusion is that the use of an oil soluble thiol indicator, if compartmentalized in an oil emulsion, permits the use of enzymes which are commonly believed to be sensitive to thiol reagents.

b. EA1 deposited directly into paper.

EA1 was dissolved in toluene to a concentration of 5.7 mM. Whatman 31 ET paper was impregnated with this solution and dried at 50°. A second solution was prepared of the following constituents:

|  | Final Concentration |
|---|---|
| Triton ® X-100 | 0.1% |
| (tris)$_2$ sulphate pH 8.5 | 0.2 M |
| PVA (98.5% hydrolysed) | 0.62% |
| MPMS | 0.25 μM |
| Lipoamide | 0.25 mM |
| LipDH | 30 U/mL |
| NAD | 0.5 mM |
| DCIP | 0.8 mM |

(Tris)$_2$ sulphate is tris buffer adjusted to the desired pH with sulfuric acid.

The dried paper was dipped into the second solution and dried again at 50° C. and affixed to a plastic support.

Test solutions for LDH contained L-lactate (167 mM), (tris)$_2$ sulphate, pH 8.5, (0.33M) and LDH enzyme (rabbit muscle, Sigma type II), as shown in the following table with the test results.

| Time (minutes) | LDH Concentration (μ/mL) | | | | |
|---|---|---|---|---|---|
|  | 0 | 0.333 | 0.666 | 1.667 | 3.333 |
| 3 | dark blue | mid-blue | pale blue | blue/green | mustard |
| 4 | dark blue | mid-blue | very pale blue | bluish yellow | yellow |

Very good color discrimination is seen between the various levels of LDH.

Test Solution for alcohol detection

The ability of this compartmentalized film format to handle assays requiring the use of an enzyme which is sensitive to thiol reagents was further tested using alcohol dehydrogenase.

Test solutions were prepared which contained various concentrations of ethanol, (tris)$_2$ sulphate buffer, 0.5M, pH 8.5, and alcohol dehydrogenase (from Baker's yeast, Sigma Catalog #A7011, 22.5 U/mL).

The test strips prepared as described above were used. The results are shown in the following table.

| Time (minutes) | Ethanol Concentration (mg/dL) | | | | | |
| --- | --- | --- | --- | --- | --- | --- |
| | 0 | 1.84 | 3.22 | 4.6 | 6.9 | 11.5 |
| 3 | dark blue | less blue | medium blue | pale blue | blue/green | mustard |
| 4 | dark blue | less blue | medium blue | pale blue | mustard | yellow |

Very good discrimination was seen between levels of alcohol.

From these experiments it was concluded that the RAINBOW system utilizing a thiol detection reagent can be used with thiol reagent sensitive enzymes.

B. Approach 2: Physical separation of thiol reagent sensitive enzyme and thiol reagent by immobilizing the latter.

DTNB can be covalently bound to a large molecule or can be physically trapped in a matrix, such as gelatin, which only allows penetration of small molecules. Therefore direct interaction between the enzyme and thiol reagent would not be expected.

Preparation of immobilized DTNB

DTNB was linked to human serum albumin through the carboxyl function using a water soluble carbodiimide reagent as shown below.

A 30% human serum albumin solution was made 0.2M in sodium phosphate and the pH adjusted to 4.57. It was then diluted to 4.8% albumin. DTNB (10.7 mM) and 1-ethyl-3-(3-dimethylaminopropyl) carbodiimide (EDAC, 10.7 mM) were dissolved in a small amount of ethanol and added, with vigorous stirring, to the albumin solution maintained at 0° C. After 2 to 3 hours, the lightly gelled material was transferred to dialysis tubing and dialysed extensively against water. Then it was lyophilized.

The crusty yellow solid was pulverized to a fine powder and dispersed in 10% gelatin to a concentration of 1%. A coating was made, and dried at room temperature.

The film was evaluated with the following test mixture:

|  | Final Concentration |
| --- | --- |
| lithium lactate | 250 mM |
| potassium phosphate buffer, pH 7.5 | 250 mM |
| glutathione | 0.5 mM |
| glutathione reductase | 9 U/mL |
| NAD | 0.2 mM |
| LDH | 5 U/mL |

When contacted with this solution, the film produced a clear yellow color within one minute. A control solution, without LDH, produced no color.

The conclusion is that immobilizing the thiol reagent allows assay with thiol reagent sensitive enzymes.

The overall conclusion is that although many enzymes, such as alcohol dehydrogenase and cholesterol dehydrogenase are inhibited by DTNB according to the literature, there are many ways of avoiding this inhibition. Consequently a second catalytic system which involves thiol indicators is generally applicable to assay of NADH as an intermediate and could be used to determine alcohol or cholesterol as analytes.

EXAMPLE 6

Diffusible/Nondiffusible Dye Reaction another approach to generating a RAINBOW is where the hue of the test composition is made to visible to the user as a result of diffusion. For instance, if a indicator is unable to diffuse due to being covalently linked to a matrix, and this matrix is covered with an opaque layer, then the indicator will be invisible from the top. If, as a result of a reaction, the covalent linkage of the indicator to the matrix is severed, then the indicator can diffuse up through the opaque covering and become visible.

As an example, a film was prepared as described in Example 5B, where DTNB was covalently bound to albumin and was then incorporated into a gelatin matrix. Whatman 31 ET was impregnated with a solution containing:

|  | Final Concentration |
| --- | --- |
| potassium phosphate, pH 7.5 | 160 mM |
| glutathione | 0.4 mM |
| gluthathione reductase | 36 U/mL |

The impregnated paper was dried at 50° C. Pieces of the dried paper were cut and laid on the gelatin film. The paper was quite opaque. An NADH solution was added to the multilayer device prepared in this way and water to another device to be used as a control. Within approximately 20 seconds, the device contacted with NADH began to turn yellow and rapidly developed to a deep yellow. The control pad had no color.

An LDH assay was made with the following solution:

|  | Final Concentration |
| --- | --- |
| potassium phosphate, pH 7.5 | 250 mM |
| lithium lactate | 250 mM |
| NAD | 0.2 mM |

LDH (about 5 U/mL) was added to this solution and 30 μL of the solution was added to one of the multilayer paper/gelatin device described above.

After about 5½ minutes, the LDH pad showed a faint but definite yellow color. The control, without LDH, had no color.

The conclusion is that indicators can indeed be made diffusible as a function of analyte concentration.

In this approach, the indicator molecule is a combination of a hue determining (chromophoric) part and reactive (cleavable) part. These can be electronicallly isolated such that cleavage of the anchoring linkage does not significantly change the hue of the indicator. The amount, or intensity, of the indicator can be controlled by the activity of the catalytic system involved in the reductive cleavage and the hue which is generated is determined independently by the chromophoric part of the molecule. This is a considerable advantage as it can be difficult to find indicators with a suitable combination of hue and respectively to generate the desired final hue.

Other matrices to which a thiol indicator could be immobilized by oxidation are: thiolagarose or any protein using a bifunctional reagent, e.g. Lomant's reagent, dithiobis (succinimidyl propionate).

EXAMPLE 7:

glucose formulations

Glucose test devices useful for testing whole blood can be prepared as follows. Reduced nicotinamide adenine dinucleotide was the common substrate and was generated from glucose by glucose dehydrogenase. The general chemistry for RAINBOW glucose formulations is shown schematically following Example 7A. The thiol indicator, DTNB, is commonly called Ellman's Reagent.

| Layer | A. Pathway 1: Diaphorase/NBT/TR-1: Pathway 2: Lipoamide dehydrogenase/lipoamide/DTNB | |
|---|---|---|
| | Component | Quantity (g) |
| 1 | Gelatin | 1.13 |
| | Water | 6.78 |
| | PVP K30 (20%) | 1.69 |
| 2 | Triton ® X-100 (4%) | 0.40 |
| | NBT | 0.064 |
| | Gelatin | 1.13 |
| | HEPES Buffer, (1 M, pH 7.5) | 5.42 |
| | Water | 1.36 |
| | PVP K30 (20%) | 1.69 |
| | $K_3Fe(CN)_6$ | 0.073 |
| | DTNB | 0.040 |
| | GDH (64.6 U/mg) | 0.060 |
| | Diaphorase (118 U/mg) | 0.005 |
| | BSA | 0.035 |
| | Lipoamide | 0.030 |
| | LipDH (1350 U/mL) | 200 μL |
| 3 | NAD+ | 0.060 |
| | Mutarotase (5060 U/mL) | 100 μL |
| | Triton ® X-100 (4%) | 0.4 |
| | Gelatin | 1.13 |
| | Water | 6.78 |
| | Triton ® X-100 (4%) | 0.40 |
| | TR-1 | 0.060 |
| 4 | carbodiimide | 1.25% |

Procedure: The components of each solution were combined at 40° in the order given. The solutions were degassed before coating. Layer 1 was spread onto a polyester backing and dried. Layer 2 was spread onto Layer 1 and dried and so on. The final device was made up of three gelatin layers on a polyester backing. The carbodiimide treatment crosslinks the gelatin matrix thereby providing a harder surface which permits wiping the surface of the device.

Dose Response: With increasing glucose concentration from 50 to 600 mg/dL, the color sequence was pale red to olive green to blue black.

"RAINBOW" CHEMISTRY

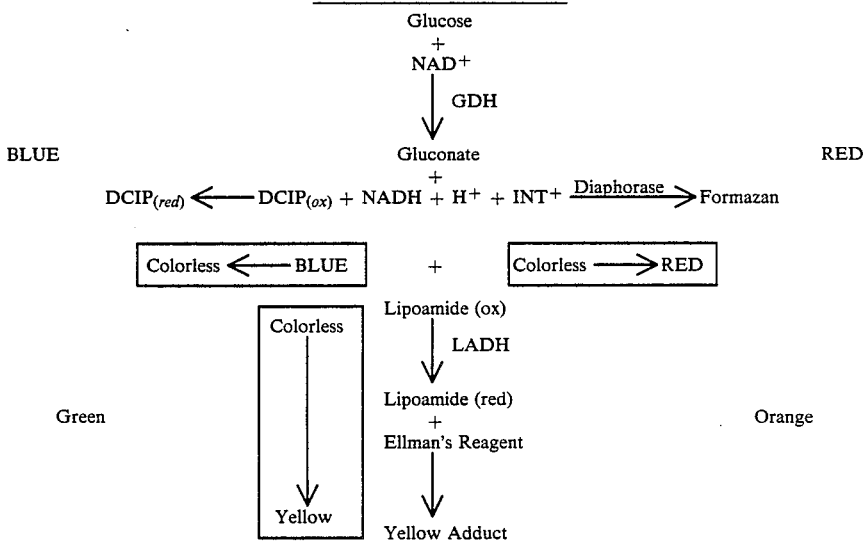

B. Pathway 1: MPMS/DCIP/INT
Pathway 2: Glutathione/Reductase/glutathione/DTNB Reductase

| Layer | Component | Quantity (g) |
|---|---|---|
| 1 | Gelatin | 1.13 |
| | Water | 6.78 |
| | PVP K30 (20%) | 1.69 |
| | Triton ® X-100 (4%) | 0.40 |
| | INT | 0.064 |
| 2 | Gelatin | 1.13 |
| | HEPES Buffer, (pH 7.5) 1 M, | 5.42 |
| | Water | 1.36 |

-continued

| Layer | Component | Quantity (g) |
|---|---|---|
|   | PVP K30 (20%) | 1.69 |
|   | Triton ® X-100 (4%) | 0.40 |
|   | DCIP | 0.0147 |
|   | K$_3$Fe(CN)$_6$ | 0.073 |
|   | DTNB | 0.040 |
|   | GDH (64.6 U/mg) | 0.060 |
|   | NAD$^+$ | 0.060 |
|   | MPMS | 0.010 |
|   | Glutathione Reductase (2320 U/mL) | 230 µL |
|   | Glutathione | 0.089 |
|   | Mutarotase (5060 U/mL) | 100 µL |
| 3 | Carbodiimide | 1.25% |

The procedure used for the formulation and testing of the device was that of Example 7A.
Dose Response:

| Glucose (mg/dL) | Color |
|---|---|
| 110 | Peacock Blue |
| 140 | Green-Blue |
| 180 | Dull Light Aqua |
| 250 | Dull Rose |
| 300 | Dull Rose |
| 400 | Rose |
| 500 | Rose |
| 600 | Dark Rose |
| 800 | Burgandy |

The colors blue to rose to burgandy can be easily distinguished visually.

C. Pathway 1: MPMS/DCIP/INT
Pathway 2: LipDH/Lipoamide/DTNB

| Layer | Component | Quantity (g) |
|---|---|---|
| 1 | Gelatin | 1.13 |
|   | Water | 6.78 |
|   | PVP K30 (20%) | 1.69 |
|   | Triton X-100 (4%) | 0.40 |
|   | INT | 0.064 |
| 2 | Gelatin | 1.13 |
|   | HEPES Buffer, 1 M, pH 7.5 | 5.92 |
|   | Water | 1.86 |
|   | PVP K30 (20%) | 1.69 |
|   | Triton ® X-100 (4%) | 0.40 |
|   | K$_3$Fe(CN)$_6$ | 0.073 |
|   | DTNB | 0.040 |
|   | GDH (64.6 U/mg) | 0.060 |
|   | NAD$^+$ | 0.060 |
|   | MPMS | 0.010 |
|   | DCIP | 0.0147 |
|   | Lipoamide | 0.030 |
|   | Mutarotase (5060 U/mL) | 100 µL |
|   | LipDH (1350 U/mL) | 200 µL |
| 3 | Carbodiimide | 1.25% |

The procedure used for the formulation and testing of the device was that of Example 7A.
Dose Response:

| Glucose (mg/dL) | Color |
|---|---|
| 20 | Peacock Blue |
| 40 | Peacock Blue |
| 70 | Aqua |
| 110 | Teal Green |
| 140 | Mint Green |
| 180 | Sea Green |
| 250 | Green Gold |
| 300 | Gold |
| 400 | Orange Gold |
| 500 | Orange |
| 600 | Dark Orange |
| 800 | Darker Orange |

The colors blue, green, gold, orange are visually distinct.

D. Pathway 1: MPMS/DCIP/INT
Pathway 2: LipDH/Lipoamide/3-ND

| Layer | Component | Quantity (g) |
|---|---|---|
| 1 | Gelatin | 1.13 |
|   | Water | 6.78 |
|   | PVP K30 (20%) | 1.69 |
|   | Triton ® X-100 (4%) | 0.40 |
|   | INT | 0.064 |
| 2 | Gelatin | 1.13 |
|   | HEPES Buffer, 1 M, pH 7.5 | 5.92 |
|   | Water | 1.86 |
|   | PVP K30 (20%) | 1.69 |
|   | Triton ® X-100 (4%) | 0.40 |
|   | K$_3$Fe(CN)$_6$ | 0.073 |
|   | DCIP | 0.0147 |
|   | 3-ND (20 mM) | 1.25 mL |
|   | GDH | 0.060 |
|   | NAD$^+$ | 0.060 |
|   | MPMS | 0.010 |
|   | Lipoamide | 0.030 |
|   | Mutarotase (5060 U/mL) | 100 µL |
|   | LipDH (1350 U/mL) | 200 µL |
| 3 | Carbodiimide | 1.25% |

The procedure used for the formulation and testing of the device was that of Example 7A.
Dose Response:

| Glucose (mg/dL) | Color |
|---|---|
| 40 | Peacock Blue |
| 70 | Teal Green |
| 110 | Mint Green |
| 140 | Light Mint |
| 180 | Sea Green |
| 250 | Tan |
| 300 | Dark Tan |
| 400 | Pale Brown |
| 500 | Rust |
| 600 | Rust |
| 800 | Dark Red |

With this formulation, using the DTNB derivative 3-ND, the generation of the final hue of the test device, visible to the user, was complete in 8 minutes.

E. Pathway 1: MPMS/DCIP/INT
Pathway 2: LipDH/lipoamide/3-ND

| Layer | Component | Quantity (g) |
|---|---|---|
| 1 | gelatin | 1.13 |
|   | water | 6.78 |
|   | PVP K30 (20%) | 1.69 |
|   | Triton ® X-100 (4%) | .40 |
|   | INT | .064 |
| 2 | gelatin | 1.13 |
|   | HEPES Buffer, 1 M pH = 7.5 | 5.92 |

-continued

| Layer | Component | Quantity (g) |
|---|---|---|
| | water | 1.86 |
| | PVP K30 (20%) | 1.69 |
| | Triton ® X-100 (4%) | .40 |
| | 3-ND (40 mM) | 2.50 mL |
| | DCIP | 0.0147 |
| | GDH | 0.060 |
| | NAD+ | 0.060 |
| | MPMS | 0.010 |
| | lipoamide | 0.030 |
| | mutarotase (5060 U/mL) | 100 μL |
| | LipDH (1350 U/mL) | 200 μL |
| | K$_3$Fe(CN)$_6$ | 0.55 |
| 3 | carbodiimide | 1.25% |

The procedure used for the formulation and testing of the device was that of Example 7A.

Dose Response:

| Glucose mg/dL | Hue generated |
|---|---|
| 0 | blue |
| 20 | dark blue green |
| 40 | blue green |
| 70 | light green |
| 110 | yellow green |
| 140 | gold |
| 180 | gold orange |
| 250 | orange |
| 400 | red orange |
| 800 | deep red |

This device exhibits a full spectrum RAINBOW; blue, green, gold, orange and red. The hue visible to the user depends on the concentration of glucose and is generated in 7 to 8 minutes.

F. Whole blood glucose RAINBOW test device.
Pathway 1: Diaphorase/DCIP/INT
Pathway 2: LipDH/lipoamide/3-ND

| Layer | Component | Quantity (g) |
|---|---|---|
| 1 | Gelatin | 1.13 |
| | Water | 6.78 |
| | PVP K30 (20%) | 1.69 |
| | Triton ® X-100 (4%) | .40 |
| | INT | .064 |
| 2 | Gelatin | 1.13 |
| | MES buffer, 1 M (pH-6.5) | 5.92 |
| | Water | 1.86 |
| | PVP K30 (20%) | 1.69 |
| | Triton ® X-100 (4%) | .40 |
| | 3-ND (40 mM) | 2.5 mL |
| | GDH (64 U/mg) | .060 |
| | NAD+ | .060 |
| | Diaphorase (118 U/mg) | .010 |
| | BSA | .040 |
| | Mutarotase (5060 U/mL) | 100 μL |
| | LipDH (1350 U/mL) | 200 μL |
| | DCIP | 0.0147 |
| | K$_3$Fe(CN)$_6$ | 0.055 |
| 3 | Carbodiimide | 1.25% |

The procedure used for formulation of the device was that described in Example 7A. Testing was done with whole blood samples spiked to the desired glucose levels, analyzed with a YSI glucose analyzer. The dose response data is given below. The test device, containing a test composition of the invention compartmentalized by layering in a gelatin carrier, exhibited a full spectrum RAINBOW over a glucose concentration of 0 to 800 mg/dL. The composition was designed to produce a green hue covering the normal blood glucose range.

Dose Response:

| Glucose mg/dL | Hue Generated |
|---|---|
| 0 | blue |
| 40 | light blue |
| 70 | blue green |
| 110 | sea green |
| 140 | pale green |
| 180 | light yellow |
| 250 | yellow orange |
| 400 | orange red |
| 800 | red |

EXAMPLE 8:

Paper RAINBOW

Although multilayered gelatin is a preferred matrix for a rainbow device, a device can be prepared using paper as a carrier. A solution of the following composition, made in the order shown, was prepared.

| Time (minutes) | NADH Concentration (mM) | | | | |
|---|---|---|---|---|---|
| | 0 | .33 | 1 | 3.33 | 10 |
| 1 | blue | light blue | blue/green | brown | brown/orange |
| 2 | blue | light blue | pale green | brown | orange |
| 3 | blue | light blue | faint green | brown | orange |

The buffer was TAPSO, pH 7.4. Both polyvinylalcohol (PVA) and the order of reagent addition were critical in this example. A concentration of 1 to 1.5% PVA prevents the coprecipitation of DCIP and INT in a paper matrix.

Whatman 31 ET paper was impregnated with this solution and dried at 50° C. The dried paper was cut and mounted on a plastic backing to form test strips. The test strips were assayed with NADH solution and the results shown below.

| Reagent | PVA | Triton X-100 | Buffer | INT | DCIP | DTNB |
|---|---|---|---|---|---|---|
| Concentration (mM) Stock Solution | 10 | 10 | 1000 | 5 | 5 | 10 |
| Volume (μL) Used | 750 | 100 | 1000 | 1500 | 900 | 1500 |
| Final Concentration (mM) | 1.24 | 0.17% | 166 | 1.24 | 0.74 | 0.68 |
| Order of Mixing | 1 | 2 | 3 | 4 | 5 | 6 |

| Reagent | MPMS | Gluthatione | Glut-Reductase |
|---|---|---|---|
| Concentration (mM) Stock Solution | 0.05 | 5 | 1790 U/mL |
| Volume (μL) Used | 30 | 150 | 112 |
| Final Concentration | 250 nM | 124 μM | 33 U/mL |
| Order of Mixing | 7 | 8 | 9 |

Many variations and modifications can be made from these examples without departing from the scope or spirit of the invention.

What is claimed is:

1. Process for determining the concentration of an analyte in a fluid sample, which process comprises:
   contacting a common substrate generating system capable of generating a common substrate by reaction with an analyte of interest, with (a) an analyte, (b) a first catalytic system capable of generating a change in hue of a first indicator component by reaction with the common substrate, and (c) a second catalytic system capable of generating a change in hue of a second indicator component by reaction with the common substrate,
   wherein the generation of the change in hues of the first and second indicator components occurs substantially simultaneously and provides different hues at different analyte concentrations, the final hue depending on the concentration of the analyte.

2. The process of claim 1 in which a color retardant is added to delay the reaction of the common substrate with a catalytic systems.

3. The test composition of claim 2 in which the color retardant is potassium ferrocyanide.

4. The test composition for the determination of the concentration of an analyte in a fluid sample, comprising:
   (a) a common substrate generating system which in the presence of an analyte in a fluid sample will generate a common substrate selected from the group consisting of adenosine triphosphate, reduced flavin adenine dinucleotide, hydrogen peroxide, glycerol and glucose;
   (b) a first catalytic system capable of generating a change in hue in a first indicator upon reaction with the common substrate; and
   (c) a second catalytic system capable of generating a change in hue in a second indicator by reaction with the common substrate,
   wherein the generation of the change in hues of the first and second indicators occurs substantially simultaneously and provides different hues at different analyte concentrations, the final hue produced by the test composition depending on the concentration of the analyte present in the fluid sample.

5. The test composition of claim 4 in which the common substrate generating system is glucose oxidase and the analyte is glucose.

6. The test composition of claim 4 in which the common substrate generating system is cholesterol oxidase and the analyte is cholesterol.

7. The test composition of claim 4 in which the common substrate generating system is alcohol oxidase and the analyte is alcohol.

8. The test composition of claim 4 in which the common substrate generating system is lipoprotein lipase and the analyte is triglyceride.

9. The test composition of claim 8 in which the first catalytic system comprises glycerolkinase and the second catalytic system comprises glycerol dehydrogenase.

10. The test composition of claim 4 in which the common substrate generating system is alpha amylase and the analyte is alpha amylase.

11. The test composition of claim 10 in which the first catalytic system comprises hexokinase and the second catalytic system comprises glucose dehydrogenase.

12. The test composition of claim 4 in which the change in hue of one of the first or second indicators is from a hue to substantially colorless.

13. The test composition of claim 4 in which a color retardant is added to the test composition to delay the reaction of the common substrate with the catalytic systems.

14. The test composition of claim 4 which also contains a buffer for maintaining the pH of the test composition between about 6 and 9.

15. The test device for the determination of concentration of an analyte in a fluid sample comprising:
   a carrier matrix, and
   a test composition incorporated into the carrier matrix, said test composition comprising:
   (a) a common substrate generating system which in the presence of an analyte in a fluid sample will generate a common substrate selected from the group consisting of adenosine triphosphate, reduced flavin adenine dinucleotide, hydrogen peroxide, glycerol and glucose;
   (b) a first catalytic system capable of generating a change in hue in a first indicator upon reaction with the common substrate; and
   (c) a second catalytic system capable of generating a change in hue in a second indicator by reaction with the common substrate,
   wherein the generation of the change in hues of the first and second indicators occurs substantially simultaneously and provides different hues at different analyte concentrations, the final hue produced by the test composition depending on the concentration of the analyte present in the fluid sample.

16. The test device of claim 15 in which at least one indicator component is compartmentalized within the carrier matrix.

17. The test device of claim 16 in which at least one indicator component is compartmentalized within a gelatin layer within a carrier matrix.

18. The test device of claim 15 in which the carrier matrix is paper.

19. The test device of claim 15 in which the carrier matrix is a hydrophilic carrier.

* * * * *

UNITED STATES PATENT AND TRADEMARK OFFICE
CERTIFICATE OF CORRECTION

PATENT NO. : 4,898,813

DATED : February 6, 1990

INVENTOR(S) : James P. Albarella, Steven C. Charlton, James W. Reinsch and Mary E. Warchal It is certified that error appears in the above-identified patent and that said Letters Patent is hereby corrected as shown below:

Column 7, lines 35-40 (drawing), $(H_3C)_2N(C_3H_6)NHCO$ should read $(H_3C)_2N(C_3H_6)HNCO$.

Column 16, line 43, the term "were" should read --was--.

Column 18, line 61, after the term "This" insert --was--.

Signed and Sealed this

Ninth Day of June, 1992

Attest:

DOUGLAS B. COMER

Attesting Officer

Acting Commissioner of Patents and Trademarks